(12) United States Patent
Izzia et al.

(10) Patent No.: US 9,121,755 B2
(45) Date of Patent: Sep. 1, 2015

(54) EMISSION AND TRANSMISSION OPTICAL SPECTROMETER

(75) Inventors: Federico Izzia, Middleton, WI (US); Michael S. Bradley, Edgerton, WI (US)

(73) Assignee: THERMO ELECTRON SCIENTIFIC INSTRUMENTS LLC, Madison, WI (US)

( * ) Notice: Subject to any disclaimer, the term of this patent is extended or adjusted under 35 U.S.C. 154(b) by 180 days.

(21) Appl. No.: 13/609,028

(22) Filed: Sep. 10, 2012

(65) Prior Publication Data

US 2013/0063714 A1    Mar. 14, 2013

Related U.S. Application Data

(60) Provisional application No. 61/532,505, filed on Sep. 8, 2011.

(51) Int. Cl.

| | |
|---|---|
| *G01J 3/02* | (2006.01) |
| *G01N 21/65* | (2006.01) |
| *G01J 3/36* | (2006.01) |
| *G01J 3/44* | (2006.01) |
| *G01J 3/453* | (2006.01) |
| *G01J 3/10* | (2006.01) |

(52) U.S. Cl.
CPC ............ *G01J 3/0202* (2013.01); *G01J 3/0235* (2013.01); *G01J 3/36* (2013.01); *G01J 3/44* (2013.01); *G01J 3/453* (2013.01); *G01N 21/65* (2013.01); *G01J 3/02* (2013.01); *G01J 3/10* (2013.01)

(58) Field of Classification Search
CPC ........... G01J 3/0202; G01J 3/036; G01J 3/44; G01J 3/0235; G01J 3/453; G01J 3/10; G01J 3/02; G01N 21/65
See application file for complete search history.

(56) References Cited

U.S. PATENT DOCUMENTS

| | | | |
|---|---|---|---|
| 5,499,095 A | | 3/1996 | Gast et al. |
| 5,553,616 A | * | 9/1996 | Ham et al. ..................... 600/316 |
| 5,841,139 A | * | 11/1998 | Sostek et al. ............. 250/339.12 |
| 6,061,134 A | * | 5/2000 | Jensen et al. .................. 356/451 |
| 2003/0094573 A1 | | 5/2003 | Lin et al. |
| 2007/0076208 A1 | * | 4/2007 | Koo .............................. 356/451 |
| 2007/0104238 A1 | * | 5/2007 | Hu et al. ..................... 372/43.01 |
| 2010/0136609 A1 | * | 6/2010 | Clay et al. ....................... 435/34 |
| 2011/0102565 A1 | | 5/2011 | Wang et al. |
| 2011/0189787 A1 | | 8/2011 | Graves |

FOREIGN PATENT DOCUMENTS

| | | | |
|---|---|---|---|
| JP | 03-172741 | * | 7/1991 |
| JP | 2002-005835 | * | 1/2002 |

OTHER PUBLICATIONS

Machine Translation of JP 03-172741.*
Machine Translation of JP 2002-005835.*

* cited by examiner

*Primary Examiner* — Yara B Green
(74) *Attorney, Agent, or Firm* — Jon C. Abraham

(57) ABSTRACT

A novel emission and transmission optical spectrometer is introduced herein, which is capable of optically interrogating solid or liquid samples of organic, inorganic or polymeric chemistry, for pharmaceutical research, forensic and liquid analyses, used for identification, purity check, and/or structural study of chemicals. The beneficial aspects of the system are a single sample compartment as confined within the walls of the spectrometer housing, a more compact accessory, and the capability of making both emission (e.g., Raman and Fluorescence) and Infrared (IR, NIR) transmission measurements at designed sample points.

16 Claims, 4 Drawing Sheets

EMISSION AND TRANSMISSION OPTICAL SPECTROMETER

CROSS-REFERENCE TO RELATED APPLICATIONS

The present application claims the priority of U.S. Provisional Patent Application Ser. No. 61/532,505, filed Sep. 8, 2011, which is incorporated herein by reference.

BACKGROUND OF THE INVENTION

1. Field of the Invention

The present invention relates to the field of optical scientific instrumentation. More specifically, the present invention relates to an optical instrument configured to perform emission (e.g., Raman and fluorescence) and transmission spectroscopy within the housing of the apparatus for identifying the chemical composition of a sample.

2. Discussion of the Related Art

Emission, e.g., Raman, and infrared (IR) transmission spectroscopy are complementary techniques capable of, if arranged appropriately, measuring the complete vibrational spectrum of a given sample. Presently, transmission and emission spectroscopy can be performed on standard optical instruments wherein, for example, the Fourier Transform Infrared (FT-IR) portion is primarily set up as a transmission instrument but because of space limitations within the sample compartment region, the emission spectroscopy portion (e.g., to include FT Raman) is often configured with the light source or sample arranged external to the housing of the instrument by way of one or more accessory units. Such resulting one or more accessories, however, can be quite bulky and require the user to move the sample from one sampling compartment to another to measure transmission and emission spectra of a single sample.

Background information on a system that overcomes sample compartment space limitations via accessories coupled external to the housing of the instrument, is described and claimed in, U.S. Pat. No. 5,499,095, entitled, "FOURIER SPECTROMETER WITH EXCHANGEABLE ENTRANCE AND EXIT PORTS ALLOWING FOR BOTH INTERNAL AND EXTERNAL RADIATION PORTS" issued Mar. 12, 1996, to Gast et al., including the following, "there are, however, a plurality of substances which cannot be prepared for a measurement with the assistance of these standard sample preparation measures. Included therein are gaseous samples, samples which must be cooled or heated, or samples whose dimensions are too large for the sample region. In order to spectroscopically measure samples of this kind it is necessary to utilize an appropriate accessory in or on which the sample can be arranged, and by means of which the measuring beam can be introduced onto the sample. Since, due to space limitations, such an accessory cannot be accommodated in the sample region of the spectrometer optics, it is necessary to position it outside of the spectrometer housing, whereby the measuring beam is guided out of the spectrometer optics."

Background information on a combined infrared/Raman microscope system using moveable components but fixing the sample position, is described and claimed in, U.S. Pat. No. 5,841,139, entitled, "OPTICAL INSTRUMENT PROVIDING COMBINED INFRARED AND RAMEN ANALYSIS OF SAMPLES" issued Nov. 24, 1998, to Sostek et al., including the following, "the present invention provides the capability of performing microscopic infrared analysis and microscopic Raman spectroscopy on the same sample, on the same microscope, without removing the sample once it is set up for analysis."

Accordingly, a need exists for an improved optical spectrometer, which can provide both transmission and emission (e.g., Raman and fluorescence) spectroscopy as provided by a single sample compartment configured to accept a more compact accessory within the confines of the housing. The present invention is directed to such a need.

SUMMARY OF THE INVENTION

The present invention is directed to an optical instrument for use in transmission and emission spectroscopy, which includes: a spectrometer housing having a single sample compartment disposed within the walls of said spectrometer housing; an accessory coupled to the single sample compartment, the accessory further comprising an excitation source configured to generate emission from a sample coupled to a first sample platform position; a second sample platform position offset from the first sample platform position so as to be configured for infrared (IR) transmission operation; an infrared (IR) source of radiation; an interferometer adapted along a designed optical path so as to modulate either the emission or the light received from the infrared (IR) source of radiation; a first optical element configured to direct to an emission detector, the emission received along the designed optical path or to direct the infrared (IR) source of light along the designed optical path; and a second optical element configured to receive directed infrared (IR) light transmitted therethrough a sample coupled to the second platform position and further adapted to direct the infrared (IR) light transmitted therethrough to one or more infrared (IR) detectors.

DETAILED DESCRIPTION

Figure 1:
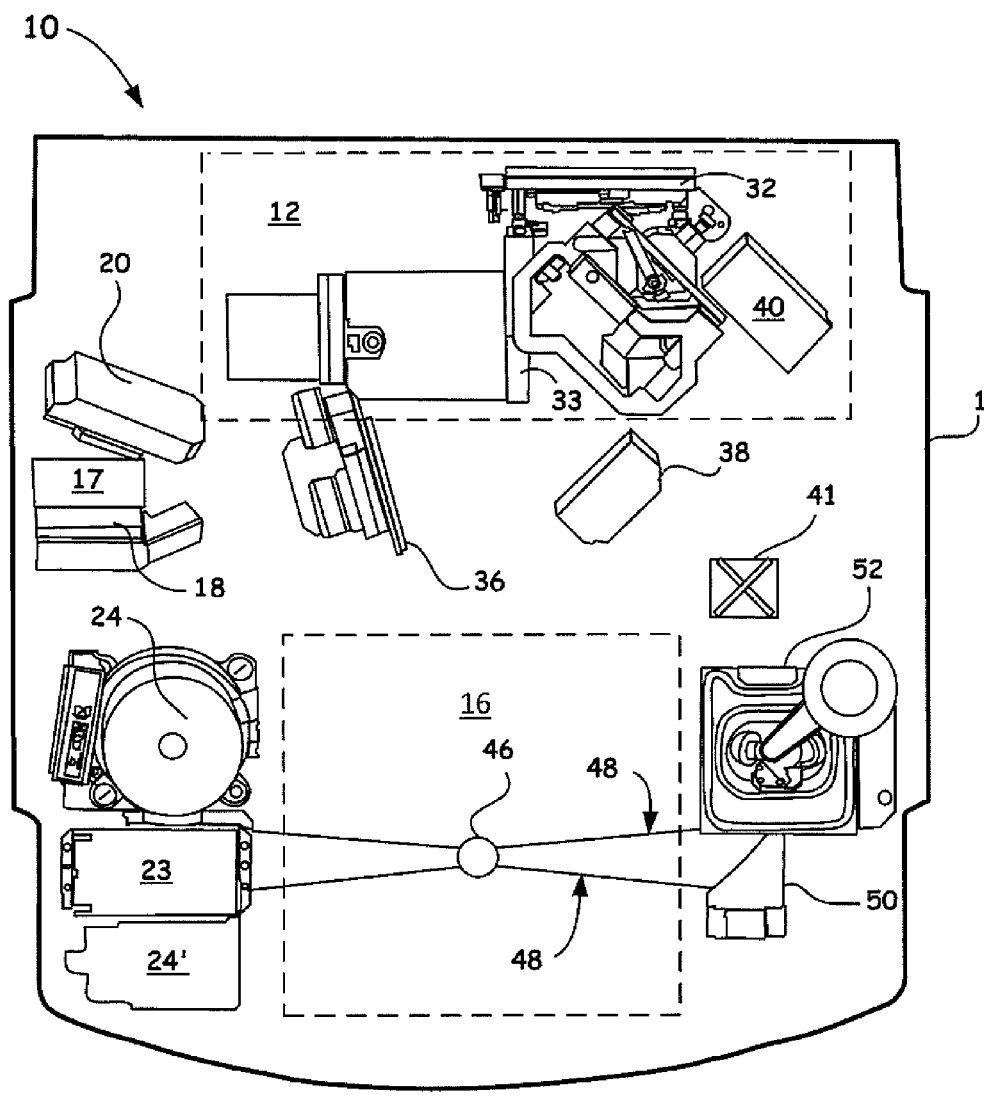
FIG. 1 shows a perspective view of a spectrometer in accordance with aspects of the present invention.

In the description of the invention herein, it is understood that a word appearing in the singular encompasses its plural counterpart, and a word appearing in the plural encompasses its singular counterpart, unless implicitly or explicitly understood or stated otherwise. Furthermore, it is understood that for any given component or embodiment described herein, any of the possible candidates or alternatives listed for that component may generally be used individually or in combination with one another, unless implicitly or explicitly understood or stated otherwise. Moreover, it is to be appreciated that the figures, as shown herein, are not necessarily drawn to scale, wherein some of the elements may be drawn merely for clarity of the invention. Also, reference numerals may be repeated among the various figures to show corresponding or analogous elements. Additionally, it will be understood that any list of such candidates or alternatives is merely illustrative, not limiting, unless implicitly or explicitly understood or stated otherwise. In addition, unless otherwise indicated, numbers expressing quantities of ingredients, constituents, reaction conditions and so forth used in the specification and claims are to be understood as being modified by the term "about."

Accordingly, unless indicated to the contrary, the numerical parameters set forth in the specification and attached claims are approximations that may vary depending upon the desired properties sought to be obtained by the subject matter presented herein. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the subject matter presented herein are approximations, the numerical values set forth in the specific examples are reported as precisely as possible. Any numerical values, however, inherently contain certain errors necessarily resulting from the standard deviation found in their respective testing measurements.

Specific Description

FIG. 1 shows a beneficial plan view of an exemplary spectrometer optical arrangement, which can be configured to measure in the infrared spectral ranges of 150-400 $cm^{-1}$ in the far IR, 400-4000 $cm^{-1}$ in the mid IR, and 4000-10000 $cm^{-1}$ in the near IR with a spectral resolution of at least 0.125 $cm^{-1}$ and with the aid of an Raman accessory, measure Raman signals in the spectral range from about 50-4000 $cm^{-1}$ with a spectral resolution better than about 0.8 $cm^{-1}$. It is however, to be noted that FIG. 1 illustrates less detail of the optical components and path, as generally designated by the reference numeral 10, but generally shows the beneficial aspects of the configuration(s) in accordance with the principles of the present invention.

Spectrometer 10 thus generally includes within the housing 1 of the spectrometer 10, a modulator, such as, but not limited to, a Michelson interferometer 12 (as denoted by the underlined reference character within the dashed box), a sample compartment 16 (also denoted by the underlined reference character within the dashed box), a first optical directional means 17 disposed therebetween an emission detector 20 (preferably a Raman detector, e.g., a liquid nitrogen-cooled NXR Genie germanium detector) and a main bench illumination source 18 (e.g., an Infrared Source (IR)), in addition to a second optical directional means 23 disposed therebetween one or more main bench emission detectors 24 and 24'.

It is to be appreciated that what is not depicted in FIG. 1 but is inclusive of the arrangement are one or more printed circuit boards containing conventional spectrometer electronics such as power supplies, signal processing circuitry, control circuitry, etc., including various discrete components, numerous wire routings, and several integrated circuits (ICs) including a computer (not shown) for controlling operation of the spectrometer in accordance with an operator's inputs. Also not shown in FIG. 1 are external optical arrangements to enable additional beneficial techniques, to include but is not just limited to, Near Infrared (NIR) and Gas Chromatography (GC) coupled accessories (not shown).

One such accessory arrangement that is, however, expressly shown in FIG. 1 is an Attenuated Total Internal Reflection (ATR) accessory 52 configured therein to accept modulated radiation from upstream components (e.g., source 18 and modulator 12). Modulated energy is thus focused by a configured objective (not shown) to a sample at a sample plane that is in contact with the bottom of a germanium hemisphere (not shown) that is typical of an ATR assembly 52. Rays that reflect from the interface between the germanium hemisphere and a sample (not shown in this context) can be redirected by, for example, flipper mirror 41 and imaged to a detector plane (not shown), which corresponds to the imaging of the sample. Therefore, because the refractive index of Ge (n=4) provides additional magnification above the nominal magnification of infrared microscopes, the Ge ATR technique enables an embodiment herein capable of collecting spectra from areas such as a 2.5×2.5 micron sample area. As an important note, the flipper mirror arrangement 41 as disposed within the housing 1 enables input/output beams when desired, such as, for example, the ATR, GC, or NIR exemplary embodiments briefly discussed above.

Also not shown in FIG. 1, but requires discussion, is a laser (e.g., a Helium Neon laser) which is energized by a laser power supply for directing a reference laser beam through and off of the configured beam-splitter of the modulator 12. In particular, the reference laser beam operates as a position clock in providing a sine wave to determine zero crossing, or zero path difference (ZPD), between the mirrors 32, 33, as shown in FIG. 1. The reference sine wave provided by the reference laser beam is used to trigger signal detection and processing circuitry for generating an interferogram of one or more samples under investigation. An accurate determination of the reference laser beam phase permits precise determination of movable component positions for accurate sampling of the beam waveforms at any desired detector position, as discussed below.

Turning back to the discussion of FIG. 1, modulator 12, in order to produce high quality interferogram data, can be configured as a scanning Michelson FTIR interferometer having a given servo control system (not shown) desirably configured to move the scanning parts, such as, one or both of the phase return mirrors 32 and 33 with a steady velocity. Velocity errors are minimized using techniques known to those of ordinary skill in the art to correct for external vibrations, such as, but not limited to, people moving, loud conversations, and noise generating equipment via a dynamic velocity control servo system when desiring best performance.

In discussing a beneficial transmission aspect of the present application, when main bench illumination source 18 is configured as an Infrared Source (IR, NIR)), described in detail below, the resultant radiation is directed as a converging beam (not shown) through a system aperture 36 via first optical directional means 17 (also to be discussed in detail below) and is received by a collimating mirror 38. The IR source itself can be a lamp or a heated infrared source chosen from any customized or conventional known source utilized in the field, such as, but not limited to, a wire, metal or ceramic element that is heated to emit a continuous band of optical radiation and coupled to the housing of the source (shown generally by the reference character 18), as known to those skilled in the art. The IR beam reflected by mirror 38 (e.g., a collimating mirror) is directed towards the beam-splitter (not distinguishable) of modulator 12.

Thereafter, portions of the IR beam transmitted through and reflected by the beam-splitter of modulator 12 are recombined at the beam-splitter and are directed as a collimated beam to a flat mirror 40. Mirror 40 directs the IR beam to a sample 46 under interrogation as configured on a platform (not shown). The IR interrogating beam is often a converging beam as enabled by mirror 50 (e.g., a parabolic mirror). The sample is disposed within a sample chamber, i.e., compartment 16 and is maintained in position by means of the sample platform (not shown). After passing through the sample 46, the diverging example IR beam is incident upon second optical directional means 23 (e.g., a parabolic mirror as discussed in detail below), which directs and focuses the IR beam onto one or more IR detectors 24 and 24' depending on the wavelength sensitivity, as additionally coupled to, and integrated with, desired circuitry (not shown). In particular, it is to be noted that the detectors 24 and 24' can comprise any detector that is capable of being used for a specific wavelength/imaging, etc. application of the present invention that can range from the ultra-violet (UV) through the Visible up to the far-infrared (IR). Example detectors include, but are not limited to, photodiodes, CCDs, liquid nitrogen cooled CCD cameras, two-dimensional array detectors, avalanche CCD photodetectors, and/or photomultipliers, and/or a photodiode capable of point-by-point scanning. It is also to be noted that any of the detectors discussed herein are directly coupled to desired signal processing circuitry designed to increase the sensitivity of the spectrometer 10 to the detected signal. In addition, any heat generated from the sources discussed herein is removed by conduction as directed into the spectrometer's base (e.g., aluminum base) for rapid and effective dissipation.

Figure 2:
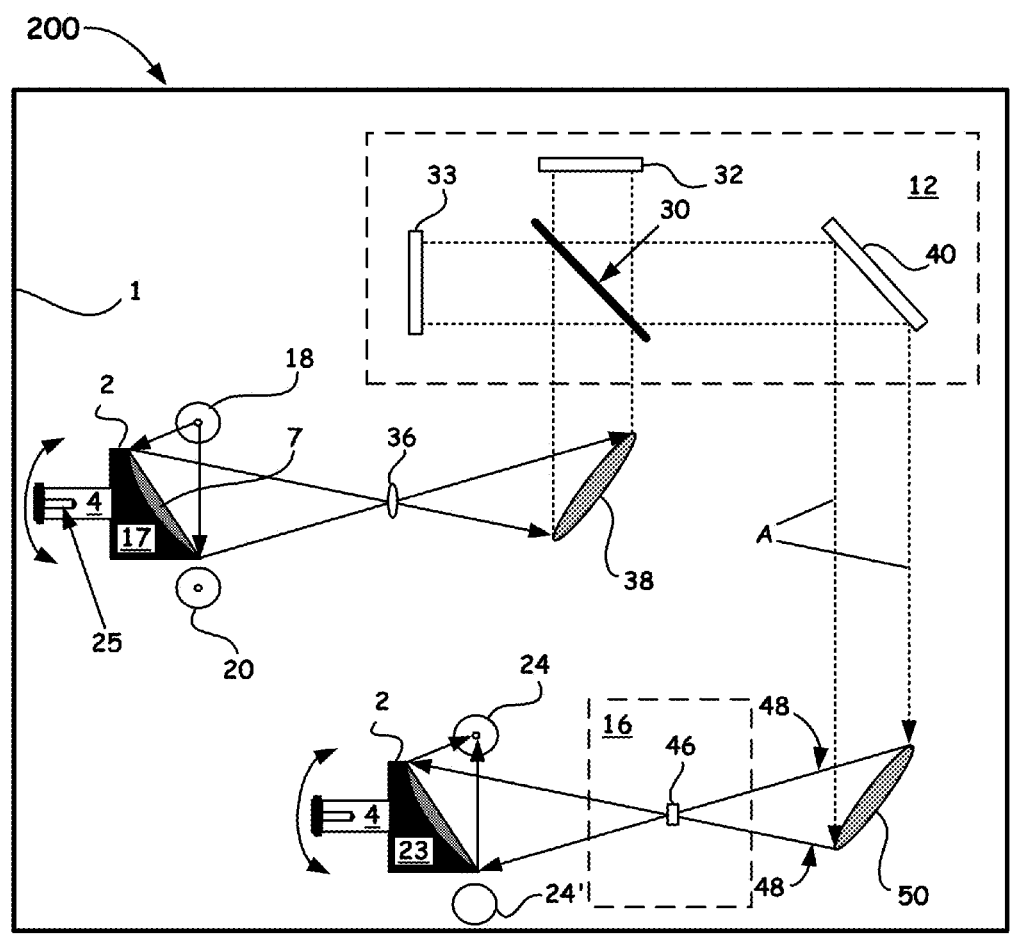
FIG. 2 shows a more generalized illustration of the transmission optical arrangement, as shown in FIG. 1.

FIG. 2 shows a more generalized drawing of the transmission optical arrangement, now generally designated by the reference numeral 200, to provide the reader with a different teaching so as to further the understanding of this aspect of the invention. The transmission aspect of the spectrometer thus generally includes (all within the housing 1 of the spectrometer), a Michelson interferometer 12 (as denoted by the underlined reference character within the dashed box), a sample compartment 16 (also again denoted by the underlined reference character within the dashed box), a first optical directional means 17 disposed therebetween an emission detector 20 (preferably a Raman detector) and a main bench illumination source 18 (e.g., a Near Infrared Source (NIR)), in addition to a second optical directional means 23 disposed therebetween one or more main bench emission detectors 24 and 24'.

The illumination IR source 18 is directed as a converging beam through a system aperture 36 via first optical directional means 17 and is received by a collimating mirror 38. The IR beam reflected by mirror 38 (e.g., a collimating mirror) is directed towards the beam-splitter 30 of modulator 12.

Thereafter, portions of the IR beam transmitted through and reflected by the beam-splitter of modulator 12 are recombined at the beam-splitter 30 and are directed as a collimated beam to a flat mirror 40. Mirror 40 directs the IR beam along beam path A to eventually be received by a sample 46 under interrogation as configured on a platform (not shown). The IR interrogating beam is often a converging beam 48 as enabled by mirror 50 (e.g., a parabolic mirror). The sample is disposed within a sample chamber, i.e., compartment 16 and is maintained in position by means of the sample platform (not shown). After passing through the sample 46, the diverging example IR beam is incident upon second optical directional means 23 (e.g., having a curved surface 7, such as, a parabolic reflective surface), which can rotate about an axis, and thus direct and focus the received IR beam onto one or more IR detectors 24 and 24' depending on a designed wavelength sensitivity as per the application.

In directing energy from a source or to alternate detectors, FIG. 2 shows the first and second optical directional means 17, 23 as rotating (as denoted by the curved double arrowed lines) monolithic geared reflector devices. However, it is to be noted that other directional devices, such as flip mirrors can also be utilized without departing from the scope of the invention. Nonetheless, the monolithic geared reflector optical design, as shown in FIG. 2 is highly desirable due to its applicability for easily directing energy from sources along a given beam path or directing received energy towards one or more predetermined detectors. Such monolithic geared reflectors 17, 23, often include a shaft 4 having a given circular cross-sectional area and an annular shaped portion 2 with integrally configured gear teeth (not shown) so as to mesh with a primary gear to provide an accurate as well as a desired rotation when coupled to a computer-coupled control means. Such a mechanism arrangement enables such rotatable devices described and utilized herein to start rotation, change rotation direction, and move with a desired rotational velocity. The reflectors 17, 23 are also embodied with a surface curvature 7 by design that can include a pair of foci $F_1$ and $F_2$ (not shown) indicative of any desired mirrored design, i.e., a design having a degree of eccentricity indicative of, for example, a parabolic, elliptical, or other surface curvature 7.

To provide mechanical support, the shaft 4 integrally configured from the geared reflector 17 and 23, as shown in FIG. 2, is provided with a hollowed portion (not specifically denoted) so as to be rotatably supported by a pin 25. The shaft 4 is also further supported by a bearing assembly (not shown) which permits shaft 4 rotation and centering with respect to a mounting flange assembly (not shown).

Figure 3:
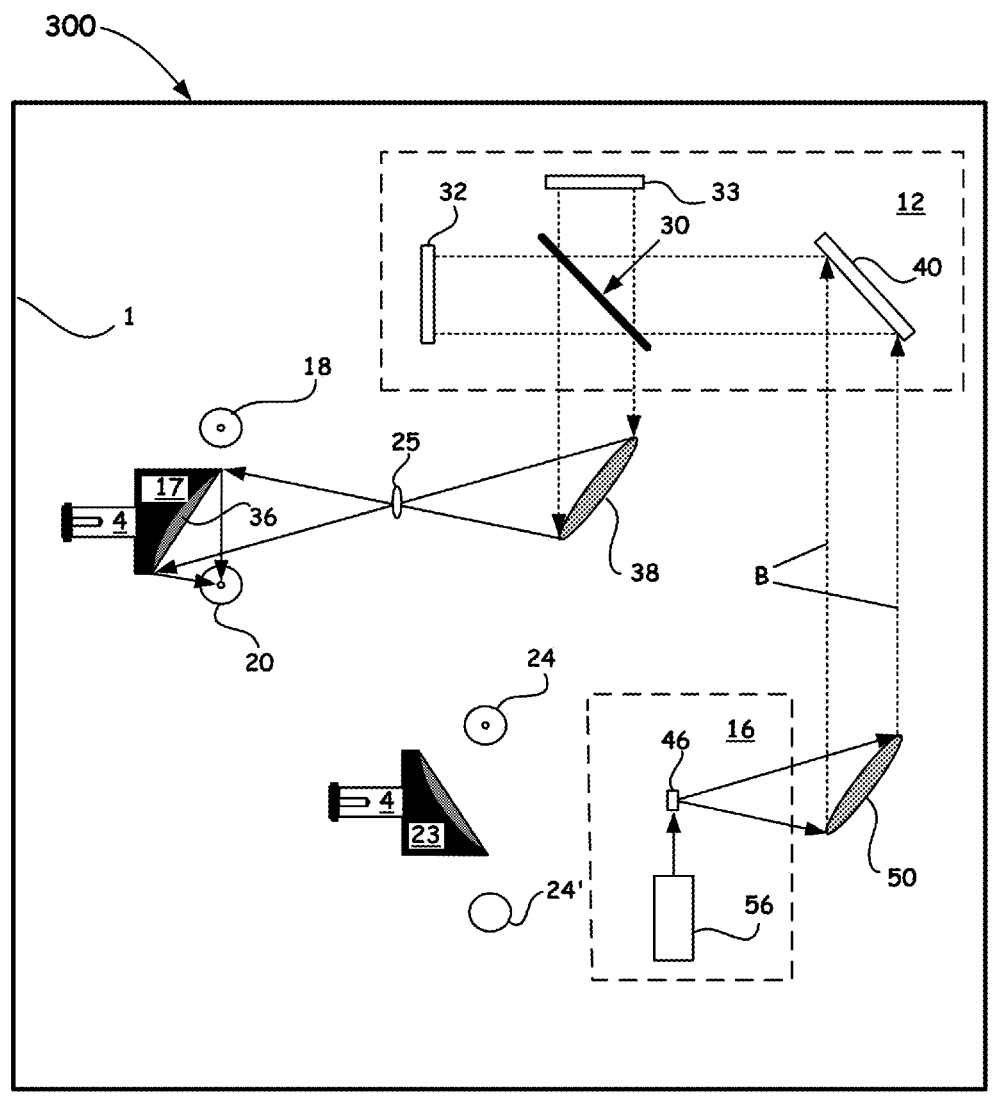
FIG. 3 shows a more generalized illustration of the emission optical arrangement, as shown in FIG. 1.

Referring to FIG. 3, such a general optical arrangement, now generally designated by the reference numeral 300, is provided to simply illustrate the emission optical aspect of the present invention, which includes an accessory that is fit into the sample compartment 16 region of the overall arrangement shown in FIG. 1. FIG. 3 thus provides to the reader a simpler understanding of the working aspects of the emission optical arrangement part of the invention using such an accessory. Accordingly, in this illustrative example, the sample 46 positioned in the sample compartment 16 is directly illuminated by light source 56, which is often a configured intense light source (e.g., a laser, such as a laser operating at 1064 nm) so as to enable, for example, fluorescence emission or Raman-scattered emission characteristic of the sample 46. An example beneficial laser source (both fiber coupled and open beam) is one that can provide wavelengths ranging from about 630 nm up to about 2400 nm.

Light emitted by the sample is thus collected by mirror 50 and directed along beam path B (as also denoted by directional arrows) so as to, if desired, be modulated in a desired manner via modulator 12, as known to those of ordinary skill in the art. In particular, portions of the emission beam are directed through and reflected by the beam-splitter 30 of modulator 12 and recombined at the beam-splitter 30 so as to be directed as a collimated beam to a mirror 38. Thereafter, such modulated light as received by mirror 38 is directed through the system aperture 25 and collected by first optical directional means 17 (e.g., a geared reflector 17 as similarly discussed above) so as to be directed to an appropriate emission detector 20 (e.g., Raman detector) for interrogation of the received light.

Figure 4:
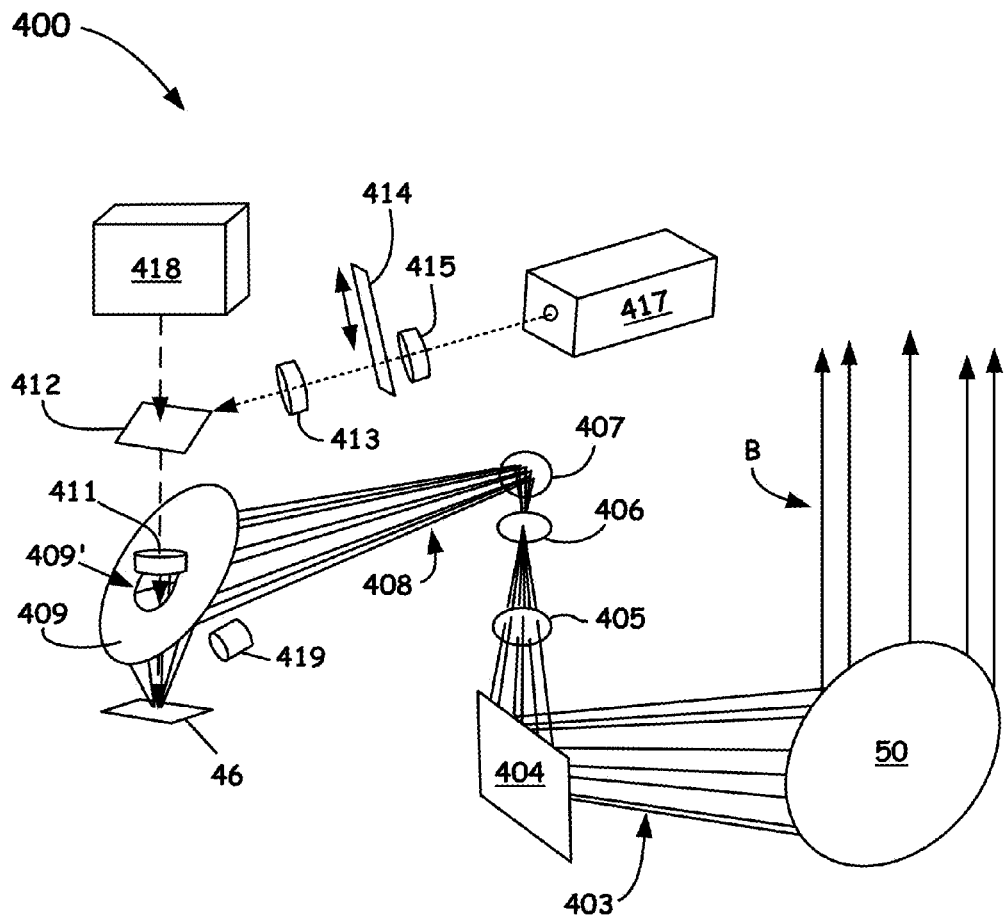
FIG. 4 shows a more a more detailed illustration of the Raman Accessory emission optical arrangement as shown in FIG. 1.

FIG. 4 is a more specific illustration of an emission (e.g., Raman) accessory embodiment, as now generally referenced by the numeral 400, which was generally shown in FIG. 3 and can be implemented into the sample compartment region 16 shown in FIG. 1 and within the confines of the walls of the housing 1. In this more detailed illustration, the intense light source 417 (i.e., a laser) can be, for example, a frequency stabilized diode laser operating at 1064 nm with at least about 500 mw of optical power in a TEM00 spatial mode. Safety shutters (not shown), such as electrically controlled solenoids connected to opaque paddles, can be open when energized and shut when appropriate. Such shutters, when operated as a pair of shutters, form a safe interlock system for the accessory

400. A bandpass filter 415 is often utilized to remove amplified stimulated emission (ASE) and other spectral artifacts from the laser 417. In addition, a variable density filter 414 is configured to move on a slide (shown with the double directional arrowed line) as driven by, for example, a stepper motor (not shown), to adjust the laser power (as shown by the lighter dashed line with an arrow) to the sample 46 mounted on sample platform offset from the sample platform used for an IR transmission configuration. This is critical, because the IR sample cannot sit in the same position as the Raman sample if the accessory is in place. Thereafter, a defocusing lens 413 can be inserted into the laser 417 beam line by, for example, a flipper mechanism (not shown) so as to allow defocusing of the laser 417 energy at the sample 46, thus reducing power density for samples that are easily burned and to provide some spatial averaging over inhomogeneous samples. The energy from laser 417 is thereafter received by a reflector 412 (e.g., a dichroic) capable of reflecting the laser light but also capable of transmitting visible light to be received by a camera 418. Also shown is a laser/video lens 411 configured to bring the laser 417 energy to a focus at the sample 46 but also capable of focusing the video camera (as shown by the heavier dashed line with an arrow) at the same sample 46 plane. A light source, such as an LED 419 (e.g., a white light LED) is arranged to illuminate the sample 46 so as to be interrogated/aligned by the video camera 418. In the light (i.e., emission) collection mode, a mirror 409, such as an off-axis parabolic mirror, with an aperture 409' in the middle collects fluorescence/Raman-scattered light. Mirror 409 causes collected emission to converge as received by mirror 407. Such emission is thereafter directed through Raleigh filters 405 and 406, e.g., edge filters, and directed to a folding mirror 404 to enable direction of such emission out of the Raman accessory, as situated within the sample compartment, as discussed above for FIG. 1. The mirror 50 (e.g., off-axis elliptical mirror) is part of the main bench optics, as also shown in FIG. 1, FIG. 2, and FIG. 3, that directs the resultant emission as a collimated beam (denoted as B) towards the modulator 12.

It is to be finally noted that the system 10, and specific components, as shown in FIG. 1, as well as other embodiments disclosed herein, are capable of being operated via a computer or processor (not shown), which may be a dedicated digital computer or digital signal processor, as known to those of ordinary skill in the art. The computer (not shown) is also often electronically coupled to one or more other output devices, such as display screens, printers, etc. and/or one or more other input devices, such as keyboards, internet connections, etc.

Thus a coupled computer or processor can orchestrate the control of moving parts, e.g., monolithic geared reflector 17 and 23 and moving mirrors configured on modulator 12, sensors, optical elements (e.g., other reflectors), and/or turn on sources, etc., as can be incorporated in the example system of FIG. 1. Instructions can also be executed as provided and stored on a machine-readable medium (e.g., a computer-readable medium). A computer-readable medium, in accordance with aspects of the present invention, refers to mediums known and understood by those of ordinary skill in the art, which have encoded information provided in a form that can be read (i.e., scanned/sensed) by a machine/computer and interpreted by the machine's/computer's hardware and/or software. In particular, the computer-readable media can often include local or remote memory storage devices, such as, but not limited to, a local hard disk drive, a floppy disk, a CD-ROM or DVD, RAM, ROM, a USB memory device, and even any remote memory storage device known and understood by those skilled in the art.

It is to be understood that features described with regard to the various embodiments herein may be mixed and matched in any combination without departing from the spirit and scope of the invention. Although different selected embodiments have been illustrated and described in detail, it is to be appreciated that they are exemplary, and that a variety of substitutions and alterations are possible without departing from the spirit and scope of the present invention.

What is claimed is:

1. An optical instrument for use in transmission and emission spectroscopy, comprising:
   a spectrometer housing having a single sample compartment disposed within the walls of said spectrometer housing;
   an accessory coupled to said single sample compartment, said accessory further comprising an excitation source configured to generate emission from a sample coupled to an emission sample platform;
   a transmission sample platform offset from said emission sample platform so as to be configured for infrared (IR) transmission operation;
   an infrared (IR) source of radiation;
   an interferometer adapted along a designed optical path so as to modulate either said emission or the light received from said infrared (IR) source of radiation;
   a first optical element configured to direct to an emission detector, the emission received along said designed optical path or to direct said infrared (IR) source of light along said designed optical path; and
   a second optical element configured to receive directed infrared (IR) light transmitted therethrough a sample coupled to said transmission sample platform and further adapted to direct said infrared (IR) light transmitted therethrough to one or more infrared (IR) detectors.

2. The optical instrument of claim 1, wherein said excitation source configured with said accessory comprises a source configured to provide emission wavelengths from about 630 nm up to about 2400 nm.

3. The optical instrument of claim 2, wherein said excitation source configured with said accessory comprises diode laser configured to provide an emission wavelength at about 1064 nm.

4. The optical instrument of claim 1, wherein said emission induced via interaction of optical light received from said excitation source with said sample coupled to the emission sample platform comprises at least one induced emission selected from: fluorescence and Raman light.

5. The optical instrument of claim 1, wherein said accessory further comprises a neutral density filter to adjust the power resultant from said excitation source.

6. The optical instrument of claim 1, wherein said accessory further comprises a defocusing lens configured with said excitation source so as to reduce the power density at said sample coupled to said emission sample platform.

7. The optical instrument of claim 1, wherein said accessory further comprises a desired bandpass filter to remove amplified stimulated emission and spectral artifacts.

8. The optical instrument of claim 1, wherein said accessory further comprises a white light illumination source configured to enable interrogation of said sample coupled to said emission sample platform or alignment of said sample coupled to said emission sample platform to enable emission to be directed along said desired optical path.

9. The optical instrument of claim 1, wherein said accessory further comprises one or more edge filters to enable a desired filtered emission to be directed by a predetermined folding optic out of said accessory and along said designed optical path.

10. The optical instrument of claim 1, wherein said one or more infrared (IR) detectors comprise at least one detector selected from: photodiodes, CCDs, liquid nitrogen cooled CCD cameras, two-dimensional array detectors, avalanche CCD photodetectors, photomultipliers, and a photodiode capable of point by point scanning.

11. The optical instrument of claim 1, wherein said emission detector comprises a Raman detector.

12. The optical instrument of claim 11, wherein said Raman detector comprises a germanium detector.

13. The optical instrument of claim 1, wherein said first and said second optical element further comprises a geared reflector.

14. The optical instrument of claim 13, wherein said geared reflector further comprises an optical reflective surface having at least one surface selected from: an elliptical surface, a parabolic surface, a toroidal surface, and a flat surface.

15. The optical instrument of claim 1, wherein said optical instrument is configured to measure in the infrared spectra ranges of 150 cm$^{-1}$ to about 400 cm$^{-1}$ in the far infrared (IR), and from about 400 cm$^{-1}$ to about 4000 cm$^{-1}$ in the mid infrared (IR), and from about 4000 cm$^{-1}$ to about 10000 cm$^{-1}$ in the near infrared with a spectral resolution of at least about 0.125 cm$^{-1}$.

16. The optical instrument of claim 1, wherein said optical instrument via the aid of said accessory is configured to measure Raman signals in the range from about 50 cm$^{-1}$ to about 4000 cm$^{-1}$ with a spectral resolution of at least about 0.8 cm$^{-1}$.

* * * * *

UNITED STATES PATENT AND TRADEMARK OFFICE
CERTIFICATE OF CORRECTION

PATENT NO. : 9,121,755 B2
APPLICATION NO. : 13/609028
DATED : September 1, 2015
INVENTOR(S) : Federico Izzia et al.

It is certified that error appears in the above-identified patent and that said Letters Patent is hereby corrected as shown below:

On patent Title page, in Item (74) Attorney, Agent, or Firm, please replace "Jon" with --Ion--.

IN THE CLAIMS

In column 9, line 23 of claim 15, please replace "400 cm-l" with --400 cm-1--.

Signed and Sealed this
First Day of March, 2016

Michelle K. Lee
*Director of the United States Patent and Trademark Office*